United States Patent
Miyamoto et al.

(10) Patent No.: US 11,298,298 B2
(45) Date of Patent: Apr. 12, 2022

(54) METHOD FOR PRODUCING NONAQUEOUS COMPOSITION FOR EXTERNAL USE ON SKIN

(71) Applicants: CHANEL PARFUMS BEAUTE, Neuilly sur Seine (FR); KYUSHU UNIVERSITY, NATIONAL UNIVERSITY CORPORATION, Fukuoka (JP)

(72) Inventors: Masayoshi Miyamoto, Funabashi Chiba (JP); Yoshihito Oda, Funabashi Chiba (JP); Masahiro Goto, Fukuoka (JP)

(73) Assignees: CHANEL PARFUMS BEAUTE, Neuilly sur Seine (FR); KYUSHU UNIVERISTY, NATIONAL UNIVERSITY CORPORATION, Fukuoka (JP)

( * ) Notice: Subject to any disclaimer, the term of this patent is extended or adjusted under 35 U.S.C. 154(b) by 0 days.

(21) Appl. No.: 16/753,396

(22) PCT Filed: Oct. 5, 2018

(86) PCT No.: PCT/EP2018/077087
§ 371 (c)(1),
(2) Date: Apr. 3, 2020

(87) PCT Pub. No.: WO2019/068847
PCT Pub. Date: Apr. 11, 2019

(65) Prior Publication Data
US 2020/0306148 A1    Oct. 1, 2020

(30) Foreign Application Priority Data
Oct. 6, 2017 (JP) .............................. JP2017-195949

(51) Int. Cl.
| | |
|---|---|
| *A61K 8/02* | (2006.01) |
| *A61K 8/04* | (2006.01) |
| *A61K 8/37* | (2006.01) |
| *A61Q 19/00* | (2006.01) |

(52) U.S. Cl.
CPC ............ *A61K 8/0291* (2013.01); *A61K 8/044* (2013.01); *A61K 8/375* (2013.01); *A61Q 19/00* (2013.01); *A61K 2800/262* (2013.01); *A61K 2800/31* (2013.01); *A61K 2800/413* (2013.01); *A61K 2800/82* (2013.01)

(58) Field of Classification Search
None
See application file for complete search history.

(56) References Cited

U.S. PATENT DOCUMENTS 10,034,834 B1    7/2018    Anderson

FOREIGN PATENT DOCUMENTS

| EP | 1 785 131 A1 | 5/2007 |
|---|---|---|
| JP | 2009-84293 A | 4/2009 |
| JP | 2011-20963 A | 2/2011 |
| WO | 2016/098857 A1 | 6/2016 |

OTHER PUBLICATIONS

Piao et al., "Preparation of a solid-in-oil nanosuspension containing I-ascorbic acid as a novel long-term stable topical formulation", International Journal of Pharmaceutics, 420, (2011), pp. 156-160. (Year: 2011).*
Mitsubishi, "SURFHOPE™SE COSME", https://www.mfc.co.jp/english/se_cosme/secosme.htm, accessed Apr. 24, 2021 (Year: 2021).*
"Palisade Layer", Merriam-Webster Dictionary, https://www.merriam-webster.com/dictionary/palisade%20layer, accessed Nov. 9, 2021 (Year: 2021).*
International Search Report dated Dec. 11, 2018 in corresponding International application No. PCT/EP2018/077087; 4 pages.

* cited by examiner

*Primary Examiner* — Melissa L Fisher
(74) *Attorney, Agent, or Firm* — Maier & Maier, PLLC

(57) ABSTRACT

A method for producing a nonaqueous composition for external use on the skin including a strongly hydrophilic amphiphilic solid active ingredient-surfactant complex dissolved or dispersed in an oil phase, the method including the steps of: dissolving a surfactant in an oil phase to obtain a surfactant solution; mixing the obtained surfactant solution with a strongly hydrophilic amphiphilic solid active ingredient to obtain a suspension; and allowing the obtained suspension to stand still to obtain a transparent composition. Unlike conventional methods for preparing S/O formulations, the strongly hydrophilic amphiphilic solid active ingredient can be solubilized in an oil phase without the process of emulsification and freeze drying.

7 Claims, No Drawings

METHOD FOR PRODUCING NONAQUEOUS COMPOSITION FOR EXTERNAL USE ON SKIN

FIELD

The present invention relates to a method for producing a nonaqueous composition for external use on the skin.

BACKGROUND

Water-soluble or hydrophilic solid active ingredients are compounds that physicochemically have high solubility in water and are largely distributed to water phases in aqueous formulations or systems consisting of water/oil, such as emulsions. The water-soluble or hydrophilic solid active ingredients are easily handleable compounds in prescription as mentioned above, whereas these compounds are known to be low transdermally absorbable via the horny cell layer due to their hydrophilic property, which is a property unfavorable for delivery to a site where their functions are exerted.

In general, the design of bases for external use requires taking into consideration the distribution coefficient between a base and the skin (horny cell layer), the activity coefficient of an ingredient in the base, and the diffusion of the ingredient in the horny cell layer. That is, for example, contrivance to the formulation of bases, chemical modification (prodrug production) which imparts lipophilicity to compounds by modification with alkyl chains, and combined use with absorption promoters are performed in order to improve the transdermal absorption of ingredients.

However, the introduction of alkyl chains to compounds, albeit contrary to its effectiveness, is known to bring about crystallization or elevation in melting point, which is unfavorable for the quality assurance of compositions for external use on the skin, such as drugs, quasi drugs and cosmetic products. Furthermore, compounds modified with alkyl chains have surface activity and the ability to self-assemble, etc., because of their amphiphilic property. Therefore, these compounds may assume an unintended form and are known to have a property unfavorable for base design. Moreover, it is also known that the stability of an active ingredient itself contained in an aqueous formulation is reduced by the hydrolysis of the chemically modified moiety.

Meanwhile, formulations based on the S/O technique which involves coating a water-soluble or hydrophilic solid active ingredient with a molecular film of a surfactant to thereby disperse the water-soluble or hydrophilic solid active ingredient as a fine particle in an oil phase are known (e.g., Japanese Patent No. 4349639 (Patent Document 1) and Japanese Patent No. 4843494 (Patent Document 2)).

However, in such a conventional S/O formulation, the water-soluble or hydrophilic solid active ingredient is present in the inside (core moiety) of the molecular film of a surfactant. Therefore, the particle size tends to be increased according to the amount of the active ingredient included, as compared with a micelle of the surfactant alone. As the amount of the surfactant is increased, the particle size is decreased. This deteriorates texture when used due to stickiness derived from the surfactant, etc. On the other hand, as the amount of the surfactant is decreased, trade-off relation is known, i.e., texture when used is improved whereas the particle size is increased or stability is deteriorated.

CITATION LIST

Patent Document

[Patent Document 1] Japanese Patent No. 4349639
[Patent Document 2] Japanese Patent No. 4843494

SUMMARY

Problems to be Solved by the Invention

Any method for solubilizing, i.e., dissolving or dispersing, a solid active ingredient having amphiphilicity that renders the solid active ingredient alone soluble in water but insoluble in an oil at normal temperature and pressure (hereinafter, referred to as "strongly hydrophilic amphiphilicity"), in an oil phase has not been known so far. Under the circumstances, there is a demand for providing a nonaqueous composition for external use on the skin comprising a strongly hydrophilic amphiphilic solid active ingredient solubilized in an oil phase and a method for producing the same.

Means for Solving the Problems

The present inventors have conducted intensive studies to solve the problem mentioned above and consequently have found that a strongly hydrophilic amphiphilic solid active ingredient suspended without being dissolved in an oil phase is solubilized by mixing a solution of a surfactant dissolved in an oil phase with the strongly hydrophilic amphiphilic solid active ingredient and allowing the obtained suspension to stand still. The present inventors have further conducted studies and consequently have found that this method can form a particle having a small particle size that cannot be achieved by conventional S/O formulations.

Although not being bound by any theory, it is considered that according to this method, unlike conventional S/O formulations, wherein a water-soluble solid active ingredient forms a core-shell particle in which the solid active ingredient is coated with a molecular film of a surfactant, the strongly hydrophilic amphiphilic solid active ingredient can be dissolved or dispersed in an oil phase by forming a mixed micelle or palisade particle in which the solid active ingredient is autonomously oriented in a micelle or a palisade layer of a surfactant in terms of host-guest chemistry, or by forming a self-assembly such as a vesicle together with a surfactant. The present invention has been completed based on these findings.

That is, the present invention relates to a method for producing a nonaqueous composition for external use on the skin, shown below.

[1] A method for producing a nonaqueous composition for external use on the skin comprising a strongly hydrophilic amphiphilic solid active ingredient-surfactant complex dissolved or dispersed in an oil phase, the method comprising the steps of:
(a) dissolving a surfactant in an oil phase to obtain a surfactant solution;
(b) mixing the surfactant solution obtained in the step (a) with a strongly hydrophilic amphiphilic solid active ingredient to obtain a suspension; and
(c) allowing the suspension obtained in the step (b) to stand still to obtain a transparent composition.
[2] The production method according to [1], wherein in the step (b), the mixing is performed using a high-speed stirrer or an ultrasonic stirrer.
[3] The production method according to [1] or [2], wherein in the nonaqueous composition for external use on the skin, the strongly hydrophilic amphiphilic solid active ingredient-surfactant complex is dissolved or dispersed as a particle having a particle size of 1 nm to 100 nm in the oil phase.
[4] The production method according to any one of claims 1 to 3, wherein in the nonaqueous composition for external use on the skin, the strongly hydrophilic amphiphilic solid active ingredient-surfactant complex is dissolved or dispersed in the oil phase in such a way that the strongly hydrophilic amphiphilic solid active ingredient forms a palisade particle in which the solid active ingredient is distributed in a palisade layer of a molecular film of a surfactant, or forms a mixed micelle particle or a self-assembly such as a vesicle together with a surfactant.

[5] The production method according to any one of [1] to [4], wherein the mass ratio of the surfactant to the strongly hydrophilic amphiphilic solid active ingredient is 2 to 50 times.

[6] The production method according to any one of [1] to [5], wherein the strongly hydrophilic amphiphilic solid active ingredient is one or more selected from the group consisting of palmitoyl-L-carnitine, hydroxycitryl palmitate, ascorbyl phosphate palmitate, (ascorbyl/tocopheryl) phosphate, cyclic lysophosphatidic acid, and salts thereof.

[7] The production method according to any one of [1] to [6], wherein the surfactant is a nonionic surfactant.

[8] The production method according to any one of [1] to [7], wherein the surfactant is one or more selected from the group consisting of glycerin fatty acid ester, polyglycerin fatty acid ester, polyoxyethylene glycerin fatty acid ester, sorbitan fatty acid ester, sucrose fatty acid ester, polyoxyethylene sorbitol fatty acid ester, polyoxyethylene castor oil and hardened castor oil.

[9] The production method according to any one of [1] to [8], wherein the HLB value of the surfactant is 10 or less.

Advantages of the Invention

According to the present invention, a nonaqueous composition for external use on the skin comprising a strongly hydrophilic amphiphilic solid active ingredient dissolved or dispersed in an oil phase can be provided by a more convenient method without the process of freeze drying used in the conventional S/O technique.

DETAILED DESCRIPTION

Modes for Carrying out the Invention

In the following, the method for producing a nonaqueous composition for external use on the skin according to the present invention will be described in detail.

1. Method for Producing Nonaqueous Composition for External Use on Skin

The production method of the present invention is a method for producing a nonaqueous composition for external use on the skin comprising a strongly hydrophilic amphiphilic solid active ingredient-surfactant complex dissolved or dispersed in an oil phase, and is characterized by comprising the following steps:
(a) dissolving a surfactant in an oil phase to obtain a surfactant solution;
(b) mixing the surfactant solution obtained in the step (a) with a strongly hydrophilic amphiphilic solid active ingredient to obtain a suspension; and
(c) allowing the suspension obtained in the step (b) to stand still to obtain a transparent composition.

The method of the present invention exploits the property, of the strongly hydrophilic amphiphilic solid active ingredient, of being autonomously oriented in a micelle or a palisade layer of a surfactant in terms of host-guest chemistry, or of autonomously forming a self-assembly such as a vesicle in terms of host-guest chemistry together with a surfactant, and thereby enables the strongly hydrophilic amphiphilic solid active ingredient to be solubilized, i.e., dissolved or dispersed, in an oil phase without the process of freeze drying used in the conventional S/O technique. In the following, each step will be described.

<Step (a)>

In the step (a), a surfactant is dissolved in an oil phase to obtain a surfactant solution.

The surfactant can be used without particular limitations as long as it is acceptable for agents for external use on the skin. Examples thereof include nonionic surfactants, anionic surfactants, cationic surfactants, ampholytic surfactants, and a bile salt.

Among these, a surfactant having an HLB value of 10 or less is preferably used in the present invention. More preferably, a surfactant having an HLB value of 8 or less, and still more preferably an HLB value of 6 or less, is used. The strongly hydrophilic amphiphilic solid active ingredient-surfactant complex can be more stably dissolved or dispersed in an oil phase by using a surfactant having an HLB value of 10 or less. Here, the "HLB value" is a value that exhibits the balance between hydrophilicity and hydrophobicity (hydrophile-lipophile balance).

In one embodiment of the present invention, a nonionic surfactant is preferably used as the surfactant. Examples of the nonionic surfactant can include polyglycerin condensed ricinoleic acid ester, decaglycerin ester, glycerin fatty acid ester, polyglycerin fatty acid ester, polyoxyethylene glycerin fatty acid ester, sorbitan fatty acid ester, polyoxyethylene sorbitol fatty acid ester, polyoxyethylene castor oil, hardened castor oil, and sucrose fatty acid ester (for example, sucrose stearic acid ester, sucrose palmitic acid ester, sucrose myristic acid ester, sucrose oleic acid ester, sucrose lauric acid ester, sucrose erucic acid ester and sucrose mixed fatty acid ester).

Among these, glycerin fatty acid ester, polyglycerin fatty acid ester, polyoxyethylene glycerin fatty acid ester, sorbitan fatty acid ester, sucrose fatty acid ester, polyoxyethylene sorbitol fatty acid ester, polyoxyethylene castor oil and hardened castor oil are preferred. Particularly, an ester compound obtained from an unsaturated fatty acid such as erucic acid or oleic acid as a raw material is preferably used, and sucrose erucic acid ester, sucrose oleic acid ester, or sucrose mixed fatty acid ester comprising them is more preferred.

These surfactants may be used singly or in combinations of two or more.

The mass ratio of the surfactant to the oil phase is preferably 0.1 to 20 mass %, more preferably 0.5 to 10 mass %, and still more preferably 1.0 to 5.0 mass %.

The oil to be used in the oil phase is not particularly limited as long as the strongly hydrophilic amphiphilic solid active ingredient is not dissolved in the oil. In the case of using two or more oils in combination, two or more oils that do not dissolve the strongly hydrophilic amphiphilic solid active ingredient even if these two or more oils are mixed are preferably used.

Examples of the oil include natural oils, hydrocarbon oils, ester oils, higher alcohols, fatty acids, and silicone oils.

Examples of the natural oil include avocado oil, camellia oil, turtle oil, macadamia nut oil, corn oil, mink oil, olive oil, rapeseed oil, yolk oil, sesame oil, persic oil, wheat germ oil, camellia kissi oil, castor oil, linseed oil, safflower oil, cottonseed oil, perilla oil, soybean oil, peanut oil, tea seed oil, Torreya seed oil, rice bran oil, Chinese tung oil, Japanese tung oil, jojoba oil, jojoba seed oil, rice germ oil, meadowfoam seed oil, coconut oil, palm oil, palm kernel oil, and linoleic acid, linolenic acid, caprylic acid, capric acid, isostearic acid, hydrogenated coconut fatty acid, and coco-caprylate/caprate, which are fatty acids.

Examples of the hydrocarbon oil include paraffins (undecane, tridecane, light paraffin, liquid paraffin), isoparaffins (isodecane, isododecane, isohexadecane, light isoparaffin, hydrogenated polyisobutene), hydrogenated polydecene, squalane, pristane, squalene, cycloparaffin, and coconut alkanes, which are alkanes.

Examples of the ester oil include isononyl isononanoate, isodecyl isononanoate, isotridecyl isononanoate, ethylhexyl isononanoate, neopentyl glycol diisononanoate, tricyclodecanemethyl isononanoate, cetyl ethylhexanoate, hexyldecyl ethylhexanoate, neopentyl glycol diethylhexanoate, trimethylolpropane triethylhexanoate, isostearyl palmitate, isopropyl palmitate, trimethylolpropane triethylhexanoate, trimethylolpropane triisostearate, glyceryl tri-2-ethylhexanoate (triethylhexanoin), pentaerythrityl tetraethylhexanoate, isostearyl myristate, isopropyl myristate, isotridecyl myristate, octyldodecyl myristate, isocetyl myristate, dihexyldecyl myristate, diethyl sebacate, diethylhexyl sebacate, diisopropyl sebacate, diisopropyl adipate, diisobutyl adipate, dihexyldecyl adipate, isodecyl neopentanoate, hexyl laurate, distearyl malate, isocetyl stearate, butyl stearate, 2-ethylhexyl stearate, hexyldecyl dimethyloctanoate, decyl oleate, octyldodecyl erucate, isobutyl isostearate, isocetyl isostearate, ethyl isostearate, isopropyl isostearate, hexyldecyl isostearate, isostearyl isostearate, glyceryl tri(caprylate/caprate), glyceryl tricaprylate, diethylhexyl succinate, bisethoxy diglycol succinate, neopentyl glycol diethylhexanoate, neopentyl glycol dicaprylate, and isostearyl neopentanoate.

The higher alcohol preferably has 22 or less carbon atoms, and more preferably has 8 to 18 carbon atoms. Examples thereof include isostearyl alcohol, octyldodecanol, oleyl alcohol, decyltetradecanol, and hexyldecanol.

The fatty acid preferably has 22 or less carbon atoms, and more preferably has 6 to 20 carbon atoms. Examples thereof include oleic acid, isostearic acid, linoleic acid, linolenic acid, caprylic acid, capric acid, and hydrogenated coconut fatty acid.

Examples of the silicone oil include chain polysiloxanes (for example, dimethicone (dimethylpolysiloxane), methyl trimethicone, caprylyl methicone, phenyl trimethicone, methylphenylpolysiloxane, diphenylpolysiloxane); and cyclic polysiloxanes (for example, octamethylcyclotetrasiloxane, cyclopentasiloxane, decamethylcyclopentasiloxane, dodecamethylcyclohexasiloxane).

These oils may be used singly or in combinations of two or more.

Among these, a nonpolar or low polar oil is preferred, and a natural oil, a hydrocarbon oil, an ester oil, or a silicone oil is especially preferred.

The proportion of the oil contained in the oil phase is preferably, for example, 60 to 100 mass %. The oil may optionally contain plant extracts by oil extraction, or the like.

Also, the oil phase may contain an optional oil-soluble additive, as needed, in addition to the oil.

In the step (a), after the addition of a surfactant to an oil phase, it is preferred that the surfactant be dissolved in the oil phase by stirring or the like, as needed.

<Step (b)>

In the step (b), the surfactant solution obtained in the step (a) is mixed with a strongly hydrophilic amphiphilic solid active ingredient to obtain a suspension.

The strongly hydrophilic amphiphilic solid active ingredient can be used without particular limitations as long as the ingredient has a both of a hydrophilic group and a lipophilic group in terms of a chemical structure, exhibits an amphiphilic property, and has a physiological activity that renders the ingredient soluble in water but insoluble in an oil at normal temperature and pressure.

Among these, a strongly hydrophilic amphiphilic solid active ingredient having a lipophilic group having 8 or more carbon atoms is preferably used in the present invention. More preferably, a strongly hydrophilic amphiphilic solid active ingredient having a lipophilic group having 12 or more carbon atoms, and still more preferably 16 or more carbon atoms, is used. In one embodiment of the present invention, the lipophilic group preferably contains a saturated or unsaturated hydrocarbon group in a linear, branched, or cyclic form, or a combination thereof, having 8 or more, 12 or more, or 16 or more carbon atoms. Here, examples of the hydrocarbon group include alkyl groups, alkenyl groups, alkynyl groups, alkyldienyl groups, aryl groups, alkylaryl groups, arylalkyl groups, cycloalkyl groups, cycloalkenyl groups, and alkylcycloalkyl groups.

In the present invention, a strongly hydrophilic amphiphilic solid active ingredient having an IOB value of 1 or more is preferably used. More preferably, a hydrophilic amphiphilic solid active ingredient having an IOB value of 1 to 5, still more preferably an IOB value of 1.2 to 3, and especially preferably an IOB value of 1.2 to 1.5, is used. The strongly hydrophilic amphiphilic solid active ingredient-surfactant complex can be more stably dissolved or dispersed in an oil phase by using a strongly hydrophilic amphiphilic solid active ingredient having a lipophilic group having 8 or more carbon atoms, and having an IOB value of 1 or more. Here, the "IOB value" is calculated from the expression IV/OV using the inorganic value (IV) and organic value (OV) of a functional group of a compound, and is a value serving as the balance between inorganicity and organicity.

Specific examples of the strongly hydrophilic amphiphilic solid active ingredient preferably include, but are not limited to, one or more selected from the group consisting of palmitoyl-L-carnitine, hydroxycitryl palmitate, ascorbyl phosphate palmitate, (ascorbyl/tocopheryl) phosphate, cyclic lysophosphatidic acid, and salts thereof.

Among others, for example, palmitoyl-L-carnitine chloride, hydroxycitryl palmitate, trisodium ascorbyl phosphate palmitate, potassium (ascorbyl/tocopheryl) phosphate and cyclic lysophosphatidic acid are preferred as the strongly hydrophilic amphiphilic solid active ingredient.

These strongly hydrophilic amphiphilic solid active ingredients may be used singly or in combinations of two or more.

In the present invention, the mass ratio of the surfactant to be used in the step (a) to the strongly hydrophilic amphiphilic solid active ingredient to be used in the step (b) is preferably 2 to 50 times, more preferably 5 times or more, still more preferably 10 times or more, more preferably 20 times or less, and still more preferably 15 times or less. Furthermore, the mass ratio is preferably 5 to 20 times, more preferably 10 to 15 times. According to a preferred embodiment of the present invention, unfavorable feeling, such as stickiness, caused by use of the surfactant can be reduced because the mass ratio of the surfactant to the strongly hydrophilic amphiphilic solid active ingredient can be decreased to 50 times or less. Furthermore, the strongly hydrophilic amphiphilic solid active ingredient-surfactant complex can be efficiently produced in the later step (c) by using the strongly hydrophilic amphiphilic solid active ingredient and the surfactant in this quantitative ratio.

After the addition of a strongly hydrophilic amphiphilic solid active ingredient to the surfactant solution, the mixture can be stirred and mixed using a high-speed stirrer such as a homogenizer, or an ultrasonic stirrer, as needed, to obtain a suspension. In the present invention, the stirring and mixing are preferably performed using a high-speed stirrer or an ultrasonic stirrer because a more uniform suspension is obtained.

<Step (c)>

In the step (c), the suspension obtained in the step (b) is allowed to stand still to obtain a transparent composition. In the step (c), the strongly hydrophilic amphiphilic solid active ingredient suspended without being dissolved in the oil phase can be dissolved or dispersed in the oil phase by forming a strongly hydrophilic amphiphilic solid active ingredient-surfactant complex together with the surfactant, to obtain a transparent composition. Here, the term "transparent" refers to a state where suspended particles, precipitates or floating matter in the suspension can no longer be confirmed visually.

The time for which the suspension is allowed to stand still is a time required for the strongly hydrophilic amphiphilic solid active ingredient to be solubilized in the oil phase by forming a complex together with the surfactant, and is not particularly limited because of differing in the types of the strongly hydrophilic amphiphilic solid active ingredient and the surfactant, but is usually 1 to 14 days, preferably 2 to 10 days, and more preferably 3 to 5 days.

As mentioned above, according to a preferred embodiment of the present invention, the nonaqueous composition for external use on the skin comprising a strongly hydrophilic amphiphilic solid active ingredient-surfactant complex dissolved or dispersed in an oil phase can be obtained merely by allowing the suspension obtained in the step (b) to stand still without a freeze drying step.

Here, the "strongly hydrophilic amphiphilic solid active ingredient-surfactant complex" is not particularly limited as long as the strongly hydrophilic amphiphilic solid active ingredient and the surfactant are assembled.

According to a preferred embodiment of the present invention, the strongly hydrophilic amphiphilic solid active ingredient can be dissolved or dispersed in an oil phase by forming a mixed micelle or palisade complex particle in which the solid active ingredient is autonomously oriented in a micelle or a palisade layer of a surfactant in terms of host-guest chemistry, or by autonomously forming a self-assembly such as a vesicle together with a surfactant in terms of host-guest chemistry. As mentioned above, in the present invention, it is considered that the particle size of the particle can be decreased as compared with conventional S/O formulations because unlike conventional S/O formulations, a strongly hydrophilic amphiphilic solid active ingredient does not form a core-shell particle in which the solid active ingredient is coated with a molecular film of a surfactant, whereas the strongly hydrophilic amphiphilic solid active ingredient is dissolved or dispersed in an oil phase by forming a mixed micelle or palisade particle in which the solid active ingredient is oriented in a micelle or a palisade layer of a surfactant, or by forming a self-assembly such as a vesicle together with a surfactant.

According to a preferred embodiment of the present invention, the strongly hydrophilic amphiphilic solid active ingredient-surfactant complex can be dissolved or dispersed, in an oil phase, as a particle (micelle) having a particle size comparable with that of a micelle formed by the surfactant alone. The particle size of the strongly hydrophilic amphiphilic solid active ingredient-surfactant complex is preferably 1 nm to 100 nm, more preferably 5 nm or larger, still more preferably 10 nm or larger, more preferably 80 nm or smaller, and still more preferably 50 nm or smaller. Furthermore, the particle size of the strongly hydrophilic amphiphilic solid active ingredient-surfactant complex is preferably 5 nm to 80 nm, more preferably 10 nm to 50 nm. When the particle size of the strongly hydrophilic amphiphilic solid active ingredient-surfactant complex falls within the above range, it is expected that the permeability into the skin is further enhanced. Here, the particle size of the strongly hydrophilic amphiphilic solid active ingredient-surfactant complex is a numerical value measured using a dynamic light scattering method. In the case where the particle of the strongly hydrophilic amphiphilic solid active ingredient-surfactant complex is not spherical, the particle size of the strongly hydrophilic amphiphilic solid active ingredient-surfactant complex means the average particle size of the strongly hydrophilic amphiphilic solid active ingredient-surfactant complex.

As mentioned above, according to the present invention, the strongly hydrophilic amphiphilic solid active ingredient can be solubilized in an oil phase by an ordinary stirring operation without using a special device. Furthermore, the amount of the surfactant used for solubilizing the strongly hydrophilic amphiphilic solid active ingredient in an oil phase can be decreased. Therefore, unfavorable feeling, such as stickiness, caused by use of the surfactant can be reduced.

In the nonaqueous composition for external use on the skin obtained by the method of the present invention, the amount of the strongly hydrophilic amphiphilic solid active ingredient-surfactant complex contained in the oil phase may be adjusted by further adding an oil, as needed.

The amount of the strongly hydrophilic amphiphilic solid active ingredient-surfactant complex contained in the oil phase may be appropriately determined depending on a purpose and usage and is not particularly limited.

The nonaqueous composition for external use on the skin obtained by the method of the present invention can, as required, optionally contain ingredients in addition to the above to such an extent that the ingredients do not impair the object and effects of the present invention. For example, ingredient(s) which can be contained in compositions for external use on the skin such as drugs, quasi drugs or cosmetic products can be contained.

As the optional ingredient(s) usable in the present invention, for example, powder ingredient(s), surfactant(s), cosurfactant(s), moisturizer(s), film agent(s), thickener(s), gelatinizer(s), inorganic mineral(s), sequestering agent(s), polyhydric alcohol(s), monosaccharide(s), oligosaccharide(s), amino acid(s), plant extract(s), organic amine(s), polymer emulsion(s), antioxidant(s), oxidization prevention assistant(s), skin nutritional supplement(s), vitamin(s), bloodstream accelerant(s), sterilizer(s), antiphlogistic (antiinflammation) agent(s), cell (skin) activation agent(s), keratolytic agent(s), tonic(s), astrictive(s), whitening agent(s), UV absorber(s), fading inhibitor(s), preservative(s), buffer(s) and/or fragrance(s) can be appropriately contained as needed. These optional ingredients can be appropriately selected depending on the formulation form and usage, etc. to be aimed at.

Examples of the powder ingredients include inorganic powders (for example, talc, kaolin, mica, sericite, muscovite, phlogopite, synthetic mica, deep red mica, biotite, vermiculite, magnesium carbonate, calcium carbonate, aluminum silicate, barium silicate, calcium silicate, magnesium silicate, strontium silicate, tungstic acid metal salt, silica, zeolite, barium sulfate, magnesium sulfate, burnt calcium sulfate (plaster), calcium phosphate, fluorine apatite, hydroxyapatite, ceramic powders, metallic soaps (for example, zinc myristate, calcium palmitate, aluminum stearate, magnesium stearate), boron nitride); organic powders (for example, polyamide resin powder (nylon powder), polyethylene powder, polymethyl methacrylate powder, polystyrene powder, co-polymer resin powder of styrene and acrylic acid, benzoguanamine resin powder, polytetrafluoroethylene powder, cellulose powder); metallic powder pigments (for example, aluminum powder, copper powder), organic pigments such as zirconium, barium or aluminum lakes; and natural pigments (for example, chlorophyll, β-carotene). Here, the powder ingredients may be subjected to a hydrophobic treatment.

The surfactants may include anionic surfactants, cationic surfactants, ampholytic surfactants, lipophilic nonionic surfactants and hydrophilic nonionic surfactants.

Examples of the anionic surfactant include fatty acid soaps (for example, sodium laurate and sodium palmitate); higher alkyl sulfate salts (for example, sodium lauryl sulfate and potassium lauryl sulfate); alkylether sulfate salts (for example, triethanolamine POE-lauryl sulfate and POE-sodium lauryl sulfate); N-acyl sarcosine acids (for example, sodium lauroylsarcosinate); higher fatty acid amide sulfonates (for example, sodium N-myristoyl-N-methyl taurate, sodium cocoyl methyl tauride and sodium lauryl methyltauride); phosphate salts (sodium POE-oleyl ether phosphate, a POE-stearyl ether phosphoric acid, etc.); sulfosuccinates (for example, sodium di-2-ethylhexylsulfosuccinate, sodium monolauroyl monoethanolamide polyoxyethylene sulfosuccinate and sodium lauryl polypropylene glycol sulfosuccinate); alkyl benzenesulfonates (for example, linear sodium dodecylbenzenesulfonate, linear triethanolamine dodecylbenzenesulfonate and a linear dodecylbenzenesulfonic acid); higher fatty acid ester sulfate salts (for example, sodium cocomonoglyceride sulfate); N-acyl glutamates (for example, monosodium N-lauroyl glutamate, disodium N-stearoyl glutamate and monosodium N-myristoyl-L-glutamate); sulfated oils (for example, Turkey red oil); POE-alkylether carboxylic acids; POE-alkyl-allylether carboxylates; α-olefin sulfonates; higher fatty acid ester sulfonates; secondary alcohol sulfate ester salts; higher fatty acid alkylolamide sulfate ester salts; sodium lauroyl monoethanolamide succinates; ditriethanolamine N-palmitoyl aspartate; and sodium casein.

Examples of the cationic surfactant include alkyltrimethylammonium salts (for example, stearyltrimethylammonium chloride and lauryltrimethylammonium chloride); alkylpyridinium salts (for example, cetylpyridinium chloride); a chloride distearyldimethylammonium dialkyldimethylammonium salt; poly(N,N'-dimethyl-3,5-methylene piperidinium) chloride; alkyl quaternary ammonium salts; alkyldimethylbenzylammonium salts; alkylisoquinolinium salts; dialkylmorpholium salts; POE-alkylamine; alkylamine salts; polyamine fatty acid derivatives; amylalcohol fatty acid derivatives; benzalkonium chloride; and benzethonium chloride.

Examples of the ampholytic surfactant include imidazoline-based ampholytic surfactants (for example, sodium 2-undecyl-N,N,N-(hydroxyethylcarboxymethyl)-2-imidazoline; and a 2-cocoyl-2-imidazolinium hydroxide-1-carboxyethyloxy disodium salt); and betaine-based surfactants (for example, 2-heptadecyl-N-carboxymethyl-N-hydroxyethyl imidazolinium betaine, lauryldimethylamino acetate betaine, alkyl betaine, amide betaine, and sulfobetaine).

Examples of the lipophilic nonionic surfactant include sorbitan fatty acid esters, such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate and diglycerol sorbitan tetra-2-ethylhexylate; glyceryl polyglyceryl fatty acids, such as glyceryl monocottonseed oil fatty acid, glyceryl monoerucate, glyceryl sesquioleate, glyceryl monostearate, glyceryl α,α'-oleate pyroglutamate, and glyceryl monostearate malate; propylene glycol fatty acid esters such as monostearate propylene glycol; a hydrogenated castor oil derivative; a glycerin alkyl ether; and steareth-2.

Examples of the hydrophilic nonionic surfactant include POE-sorbitan fatty acid esters, such as POE-sorbitan monooleate, POE-sorbitan monostearate, POE-sorbitan monooleate and POE-sorbitan tetraoleate; POE sorbitol fatty acid esters, such as POE-sorbitol monolaurate, POE-sorbitol monooleate, POE-sorbitol pentaoleate and POE-sorbitol monostearate; POE-glycerin fatty acid esters, such as POE-glycerin monostearate, POE-glycerin monoisostearate and POE-glycerin triisostearate; POE-fatty acid esters, such as POE-monooleate, POE-distearate, POE-monodioleate and ethylene glycol distearate; POE-alkyl ethers, such as POE-lauryl ether, POE-oleyl ether, POE-stearyl ether, POE-behenyl ether, POE-2-octyldodecyl ether and POE-cholestanol ether; Pluronic type surfactants (e.g., Pluronic); POE-POP-alkyl ethers, such as POE-POP-cetyl ether, POE-POP-2-decyltetradecyl ether, POE-POP-monobutyl ether, POE-POP-hydrogenated lanolin and POE-POP-glycerin ether; and steareth-21.

An oil-soluble thickener can be used as the thickener. For example, solid waxes (for example, paraffin, microcrystalline wax, vaseline, ozokerite, ceresin, polyethylene, carnauba wax, candelilla wax, rice bran wax, spermaceti, bees wax shellac wax); metallic soaps (for example, calcium stearate, magnesium stearate, aluminum stearate, zinc stearate, zinc laurate, zinc myristate); dextrin derivatives (for example, dextrin palmitate, dextrin (palmitate/ethylhexanoate), dextrin (palmitate/hexyldecanoate), dextrin myristate, dextrin isostearate); inulin derivatives (for example, inulin stearate); amino acid derivatives (for example, dibutyl ethylhexanoyl glutamide, dibutyl lauroyl glutamide); cholesterol derivatives (for example, cholesteryl stearate, fatty acid (C10-30) (cholesterol/lanosterol) esters); silicone derivatives having a siloxane bond in the backbone and having silicone or polyoxyethylene cross-linked or long-chain hydrocarbon introduced to a side chain (for example, a (dimethicone/vinyl dimethicone) cross polymer, a (dimethicone/phenyl vinyl dimethicone) cross polymer, a (vinyl dimethicone/lauryl dimethicone) cross polymer); aluminum salts of double-chain long-chain alkyl phosphoric acid esters (for example, aluminum salt of dihexadecyl phosphate); lecithins; amorphous silicas; 12-hydroxystearic acid can be used.

Clay minerals such as organically-modified clay minerals may also be used as the thickener.

Examples of the polyhydric alcohol include a dihydric alcohol, such as ethylene glycol, propylene glycol, pentylene glycol, trimethylene glycol, 1,2-butylene glycol, 1,3-butylene glycol, tetramethylene glycol, 2,3-butylene glycol, pentamethylene glycol, 2-butene-1,4-diol, hexylene glycol and octylene glycol; a trihydric alcohol, such as glycerin and trimethylolpropane; a tetrahydric alcohol such as pentaerythritol (e.g., 1,2,6-hexanetriol); a pentahydric alcohol such as xylitol; a hexahydric alcohol, such as sorbitol and mannitol; a polyhydric alcohol polymer, such as diethylene glycol, dipropylene glycol, triethylene glycol, polypropylene glycol and tetraethylene glycol; dihydric alcohol alkyl ethers, such as ethylene glycol monomethyl ether and ethylene glycol monoethyl ether; dihydric alcohol alkyl ethers, such as diethylene glycol monomethyl ether, diethylene glycol monoethyl ether and diethylene glycol monobutyl ether; a dihydric alcohol ether ester, such as ethylene glycol monomethyl ether acetate and ethylene glycol monoethyl ether acetate; a glycerol monoalkyl ether, such as chimyl alcohol, selachyl alcohol and batyl alcohol; and a sugar alcohol, such as sorbitol, maltitol, maltotriose, mannitol, sucrose, erythritol, glucose, fructose, starch sugar, maltose, xylitose, and a reduced alcohol of a starch sugar.

Examples of the antioxidants include ascorbic acid and derivatives thereof such as ascorbyl palmitate and ascorbyl tetraisopalmitate; tocopherol and derivatives thereof, such as tocopheryl acetate, tocopheryl sorbate, and other esters of tocopherol; dibutyl hydroxytoluene (BHT) and butylated hydroxyanisole (BHA); gallic acid ester.

Furthermore, the composition of the present invention may also include organic and/or inorganic sunscreens.

Examples of the organic sunscreens include dibenzoylmethane derivatives such as butyl methoxydibenzoylmethane (for example, a product commercially available from HOFFMANN LA ROCHE under the trade name of Parsol 1789); cinnamic acid derivatives such as octyl methoxycinnamate (for example, a product commercially available from HOFFMANN LA ROCHE under the trade name of Parsol MCX); salicylates; para-aminobenzoic acids; β,β'-diphenylacrylate derivatives; benzophenone derivatives; benzylidenecamphor derivatives such as terephtalylidene dicamphor sulphonic acid; phenylbenzimidazole derivatives; triazine derivatives; phenylbenzotriazole derivatives; and anthranilic acid derivatives, all of which may be coated or encapsulated.

Examples of the inorganic sunscreens include pigments and nanopigments formed from coated or uncoated metal oxides. Examples of the nanopigments include titanium oxide, iron oxide, zinc oxide, zirconium oxide and cerium oxide nanopigments, which are all well-known as UV photoprotective agents.

Examples of the antiseptic agent include p-oxybenzoate ester (e.g., methylparaben and propylparaben) and phenoxyethanol.

In addition, as an optional ingredient to be used in the composition of the present invention, those mentioned in the International Cosmetic Ingredient Dictionary and Handbook, 13th Edition, 2010, published by the Personal Care Products Council, can be used.

The amounts of these optional ingredients contained are not particularly limited as long as the optional ingredients are in a range which does not impair the object of the present invention.

The nonaqueous composition for external use on the skin obtained by the method of the present invention can be preferably used in fields such as drugs, quasi drugs and cosmetic products. The nonaqueous composition for external use on the skin obtained by the method of the present invention can contain a strongly hydrophilic amphiphilic solid active ingredient in a fine state. Therefore, it is expected that the permeability into the skin of the strongly hydrophilic amphiphilic solid active ingredient can be further enhanced by using the nonaqueous composition for external use on the skin obtained by the method of the present invention. It is considered that, for example, use of the nonaqueous composition for external use on the skin obtained by the method of the present invention as an ointment or a cosmetic can bring about the effects of the strongly hydrophilic amphiphilic solid active ingredient to the utmost extent even if the solid active ingredient is contained in a small amount.

The product form of the nonaqueous composition for external use on the skin obtained by the method of the present invention is arbitrarily selectable. For example, the composition is applicable to ointments; facial cosmetic materials, quasi drugs and drugs for external use, such as a facial cleanser, an essence liquid, a milky lotion, a cream, a pack and a beauty oil; makeup cosmetic materials, such as a foundation, a lipstick and an eye shadow; body cosmetic materials, quasi drugs, and drugs for external use; and perfumeries, etc.

EXAMPLES

In the following, the present invention will be described by way of Examples and Comparative Examples but the present invention is not limited to these Examples. Note that unless stated otherwise, the composition ratio is based on the mass ratio.

Example 1

A nonaqueous composition for external use on the skin having the composition shown in Table 1 was prepared as follows. Before the test, it was confirmed that palmitoyl-L-carnitine chloride ("Hi-carnitine" manufactured by Showa Denko K.K.; the number of carbon atoms of a lipophilic group: 16, IOB value: 1.36) was dissolved in water and was not dissolved in isopropyl myristate.

(a) Sucrose erucic acid ester ("RYOTO Sugar Ester ER-290" manufactured by Mitsubishi-Chemical Foods Corp.; HLB value: 2) was dissolved in 5 mL of isopropyl myristate to obtain a surfactant solution.

(b) The surfactant solution prepared in the step (a) was mixed with palmitoyl-L-carnitine chloride ("Hi-carnitine" manufactured by Showa Denko K.K.) to obtain a suspension.

(c) The suspension prepared in the step (b) was ultrasonicated for 20 minutes and then allowed to stand still at room temperature for 1 to 2 weeks to prepare a transparent nonaqueous composition for external use on the skin.

[1] Particle Size Measurement

The particle size of particles contained in the nonaqueous composition for external use on the skin 1 week after preparation was measured by the dynamic light scattering method. Specifically, the measurement was performed on the number mode using a nanoparticle analysis system (Zetasizer Nano ZSP model manufactured by Malvern Instruments Ltd.). The results are shown in Table 1.

The particle size of a nonaqueous composition for external use on the skin containing particles of the surfactant sucrose erucic acid ester alone, which was obtained in the same way as the process of the steps (a) to (c) except that palmitoyl-L-carnitine chloride was not used, was about 2.5 nm.

[2] Stability Evaluation

The stability of the obtained nonaqueous composition for external use on the skin was visually evaluated. The evaluation criteria were as described below.

A: Transparency was maintained 7 days after preparation
B: Contents were precipitated 7 days after preparation
The results are shown in Table 1.

TABLE 1

|  | ER-290/Hi-carnitine molar ratio (time) | ER-290/Hi-carnitine mass ratio (time) | Particle size after standing still at room temperature for 1 week (nm) | Stability |
| --- | --- | --- | --- | --- |
| Example 1-1 | 18 | 50 | 4.0 | A |
| Example 1-2 | 15 | 40 | 2.6 | A |
| Example 1-3 | 11 | 30 | 2.6 | A |
| Example 1-4 | 7 | 20 | 2.6 | A |
| Comparative Example 1-1 | 4 | 10 | Not measured due to the formation of precipitates | B |
| Comparative Example 1-2 | 2 | 5 | Not measured due to the formation of precipitates | B |

As shown in Table 1, the complex of the strongly hydrophilic amphiphilic solid active ingredient palmitoyl-L-carnitine chloride and the surfactant sucrose erucic acid ester was found to have a particle size comparable with that of the particles of sucrose erucic acid ester alone, by adjusting the quantitative ratio between palmitoyl-L-carnitine chloride and sucrose erucic acid ester (Examples 1-1 to 1-4). From this, it is considered that unlike conventional S/O formulations, the strongly hydrophilic amphiphilic solid active ingredient in Examples 1-1 to 1-4 does not form a core-shell micelle, but forms a palisade or mixed micelle particle, or a vesicle-like self-assembly with the surfactant. Furthermore, the mass ratio of the surfactant to the strongly hydrophilic amphiphilic solid active ingredient can be decreased as compared with conventional S/O formulations. Therefore, unfavorable feeling, such as stickiness, caused by use of the surfactant can be reduced.

Example 2

The same operation as in the group of Example 1 was conducted using an oil for use in cosmetic products, quasi drugs and drugs instead of isopropyl myristate. The obtained nonaqueous compositions for external use on the skin were evaluated for their particle sizes and stability. The results are shown in Table 2.

TABLE 2

| | Oil | ER-290/Hi-carnitine molar ratio (time) | ER-290/Hi-carnitine mass ratio (time) | Particle size after standing still at room temperature for 2 weeks (nm) | Stability |
|---|---|---|---|---|---|
| Example 2-1 | Squalane | 18 | 50 | 3.9 | A |
| Example 2-2 | Squalane | 11 | 30 | 3.8 | A |
| Example 2-3 | Squalane | 7 | 20 | 4.6 | A |
| Example 2-4 | Jojoba oil | 18 | 50 | 4.0 | A |
| Example 2-5 | Jojoba oil | 11 | 30 | 3.8 | A |
| Example 2-6 | Jojoba oil | 7 | 20 | 3.0 | A |

As shown in Table 2, in the case of using oils other than isopropyl myristate, such as squalane and jojoba oil, which are commonly used in cosmetic products, the strongly hydrophilic amphiphilic solid active ingredient was also shown to be complexed with sucrose erucic acid ester to form fine particles, by adjusting the quantitative ratio to the surfactant sucrose erucic acid ester (Examples 2-1 to 2-6). From this, it is considered that unlike conventional S/O formulations, the strongly hydrophilic amphiphilic solid active ingredient in Examples 2-1 to 2-6 does not form a core-shell micelle, but is also dissolved or dispersed in an oil phase by forming a palisade or mixed micelle particle, or a vesicle-like self-assembly, with the surfactant.

Furthermore, the mass ratio of the surfactant to the strongly hydrophilic amphiphilic solid active ingredient can be decreased as compared with conventional S/O formulations. Therefore, unfavorable feeling, such as stickiness, caused by use of the surfactant can be reduced.

Example 3

The same operation as in the group of Example 1 was conducted using a strongly hydrophilic amphiphilic solid active ingredient for use in cosmetic products, quasi drugs and drugs instead of palmitoyl-L-carnitine chloride. The obtained nonaqueous compositions for external use on the skin were evaluated for their particle sizes and stability. The results are shown in Table 3.

TABLE 3

| | Active ingredient | ER-290/active ingredient molar ratio (time) | ER-290/active ingredient mass ratio (time) | Particle size after standing still at room temperature for 2 weeks (nm) | Stability |
|---|---|---|---|---|---|
| Example 3-1 | APPS | 21 | 50 | 29.3 | A |
| Example 3-2 | APPS | 13 | 30 | 36.1 | A |
| Example 3-3 | APPS | 8 | 20 | 114 | A |
| Example 3-4 | APPS | 4 | 10 | 122 | A |
| Example 3-5 | APPS | 2 | 5 | 277 | A |
| Example 3-6 | EPC | 28 | 50 | 2.37 | A |
| Example 3-7 | EPC | 17 | 30 | 2.69 | A |
| Example 3-8 | EPC | 11 | 20 | 267 | A |
| Example 3-9 | CyPA | 18 | 50 | 2.98 | A |
| Example 3-10 | CyPA | 11 | 30 | 21.5 | A |
| Example 3-11 | CyPA | 7 | 20 | 34.0 | A |
| Example 3-12 | CyPA | 4 | 10 | 13.3 | A |
| Example 3-13 | CyPA | 2 | 5 | 12.3 | A |
| Comparative Example 3-1 | APPS | 0.8 | 2 | Not measured due to the formation of precipitates | B |
| Comparative Example 3-2 | EPC | 6 | 10 | Not measured due to the formation of precipitates | B |
| Comparative Example 3-3 | EPC | 3 | 5 | Not measured due to the formation of precipitates | B |

TABLE 3-continued

| | Active ingredient | ER-290/active ingredient molar ratio (time) | ER-290/active ingredient mass ratio (time) | Particle size after standing still at room temperature for 2 weeks (nm) | Stability |
|---|---|---|---|---|---|
| Comparative Example 3-4 | EPC | 1 | 2 | Not measured due to the formation of precipitates | B |
| Comparative Example 3-5 | CyPA | 0.7 | 2 | Not measured due to the formation of precipitates | B |
| Comparative Example 3-6 | APPS | ER-290 absent | | Not measured due to the formation of precipitates | B |
| Comparative Example 3-7 | EPC | ER-290 absent | | Not measured due to the formation of precipitates | B |
| Comparative Example 3-8 | CyPA | ER-290 absent | | Not measured due to the formation of precipitates | B |

1) APPS: trisodium ascorbyl phosphate palmitate ("Apprecier(R)" manufactured by Showa Denko K.K.) The number of carbon atoms of a lipophilic group: 16, IOB value: 4.23
2) EPC: potassium (ascorbyl/tocopheryl) phosphate ("EPC (SENJU) (trade name)" manufactured by Senju Pharmaceutical Co., Ltd.) The number of carbon atoms of a lipophilic group: 29, IOB value: 1.55
3) CyPA: cyclic lysophosphatidic acid ("CyPA(R)" manufactured by NOF Corp.) The number of carbon atoms of a lipophilic group: 18, IOB value: 1.98 (as sodium salt)

As shown in Table 3, in the case of using a strongly hydrophilic amphiphilic solid active ingredient other than palmitoyl-L-carnitine chloride, the strongly hydrophilic amphiphilic solid active ingredient was also shown to be complexed with sucrose erucic acid ester to form fine particles, by adjusting the quantitative ratio to the surfactant sucrose erucic acid ester (Examples 3-1 to 3-13). From this, it is considered that unlike conventional S/O formulations, the strongly hydrophilic amphiphilic solid active ingredient in Examples 3-1 to 3-13 does not form a core-shell micelle, but is also dissolved or dispersed in an oil phase by forming a palisade or mixed micelle particle, or a vesicle-like self-assembly, with the surfactant.

Furthermore, the mass ratio of the surfactant to the strongly hydrophilic amphiphilic solid active ingredient can be decreased as compared with conventional S/O formulations. Therefore, unfavorable feeling, such as stickiness, caused by use of the surfactant can be reduced.

INDUSTRIAL APPLICABILITY

According to the present invention, a nonaqueous composition for external use on the skin comprising a strongly hydrophilic amphiphilic solid active ingredient solubilized in an oil phase can be produced by a convenient method. The nonaqueous composition for external use on the skin obtained by the method of the present invention is preferably used as a composition for external use on the skin, such as drugs, quasi drugs and cosmetic products.

The invention claimed is:

1. A method for producing a nonaqueous composition for external use on the skin comprising a strongly hydrophilic amphiphilic solid active ingredient-surfactant complex dispersed in an oil phase, the strongly hydrophilic amphiphilic solid active ingredient being selected from the group consisting of palmitoyl-L-carnitine, hydroxycitryl palmitate, ascorbyl phosphate palmitate, (ascorbyl/tocopheryl) phosphate, cyclic lysophosphatidic acid, and salts thereof, the method being operated in the absence of water, and comprising the steps of:
   (a) dissolving a surfactant in an oil phase to obtain a surfactant solution;
   (b) mixing the surfactant solution obtained in the step (a) with a strongly hydrophilic amphiphilic solid active ingredient to obtain a suspension; and
   (c) allowing the suspension obtained in the step (b) to stand still to obtain a transparent composition.

2. The production method according to claim 1, wherein in the step (b), the mixing is performed using a high-speed stirrer or an ultrasonic stirrer.

3. The production method according to claim 1, wherein in the nonaqueous composition for external use on the skin, the strongly hydrophilic amphiphilic solid active ingredient-surfactant complex is dispersed as a particle having a particle size of 2 nm to 100 nm in the oil phase.

4. The production method according to claim 1, wherein the mass ratio of the surfactant to the strongly hydrophilic amphiphilic solid active ingredient is 2 to 50 times.

5. The production method according to claim 1, wherein the surfactant is a nonionic surfactant.

6. The production method according to claim 1, wherein the surfactant is one or more selected from the group consisting of glycerin fatty acid ester, polyglycerin fatty acid ester, polyoxyethylene glycerin fatty acid ester, sorbitan fatty acid ester, sucrose fatty acid ester, polyoxyethylene sorbitol fatty acid ester, polyoxyethylene castor oil and hardened castor oil.

7. The production method according to claim 1, wherein the HLB value of the surfactant is 10 or less.

* * * * *